(12) United States Patent  
Nishikawa (10) Patent No.: US 8,731,828 B2  
(45) Date of Patent: May 20, 2014

(54) MOVING ROUTE PROCESSING DEVICE AND INFORMATION PROVIDING SYSTEM USING THIS MOVING ROUTE PROCESSING DEVICE

(75) Inventor: Shuichi Nishikawa, Tokyo (JP)

(73) Assignee: Mitsubishi Electric Corporation, Tokyo (JP)

( * ) Notice: Subject to any disclaimer, the term of this patent is extended or adjusted under 35 U.S.C. 154(b) by 0 days.

(21) Appl. No.: 13/390,861

(22) PCT Filed: Sep. 4, 2009

(86) PCT No.: PCT/JP2009/004385  
§ 371 (c)(1),  
(2), (4) Date: Feb. 16, 2012

(87) PCT Pub. No.: WO2011/027403  
PCT Pub. Date: Mar. 10, 2011

(65) Prior Publication Data  
US 2012/0150442 A1      Jun. 14, 2012

(51) Int. Cl.  
*G01C 21/00*      (2006.01)  
*G01C 21/34*      (2006.01)

(52) U.S. Cl.  
CPC .............. *G01C 21/00* (2013.01); *G01C 21/34* (2013.01)  
USPC ............................ 701/519; 701/409; 701/515

(58) Field of Classification Search  
CPC ................................ G01C 21/00; G01C 21/34  
USPC ......................................... 701/409, 515, 519  
See application file for complete search history.

(56) References Cited

U.S. PATENT DOCUMENTS

| 5,359,527 | A  | * | 10/1994 | Takanabe et al. ............. 701/410 |
| 5,428,545 | A  | * | 6/1995  | Maegawa et al. ............. 701/423 |
| 5,504,482 | A  | * | 4/1996  | Schreder ................. 340/995.13 |
| 6,484,093 | B1 | * | 11/2002 | Ito et al. ....................... 701/420 |
| 7,711,475 | B1 | * | 5/2010  | Cona et al. .................... 701/415 |
| 2003/0033083 | A1 | * | 2/2003 | Nakashima et al. ......... 701/211 |
| 2003/0055983 | A1 | * | 3/2003 | Callegari ...................... 709/227 |
| 2005/0075921 | A1 | * | 4/2005 | Hayes-Roth .................... 705/10 |
| 2005/0222760 | A1 | * | 10/2005 | Cabral et al. ................. 701/209 |
| 2007/0208497 | A1 | * | 9/2007 | Downs et al. ................. 701/117 |
| 2007/0239354 | A1 | * | 10/2007 | Kwon ........................... 701/210 |
| 2008/0234921 | A1 | * | 9/2008 | Groenhuijzen et al. ...... 701/118 |
| 2009/0318121 | A1 | * | 12/2009 | Marumoto ................. 455/414.1 |

FOREIGN PATENT DOCUMENTS

| JP | 9-120495 A    | 5/1997 |
| JP | 11-083531 A   | 3/1999 |
| JP | 2002-169895 A | 6/2002 |
| JP | 2003-229973 A | 8/2003 |

(Continued)

*Primary Examiner* — Calvin Cheung  
(74) *Attorney, Agent, or Firm* — Birch, Stewart, Kolasch & Birch, LLP (57) ABSTRACT

Disclosed is a moving route processing device provided with: a route data creating unit for adding date and time information showing a current date and time to position information showing a current position to create route data with timestamp; a route data recorder for recording the route data with timestamp created by the route data creating unit; a communication processing unit for acquiring predetermined data from a database connected to a network; a route comparing unit for comparing the predetermined data acquired by the communication processing unit with the route data with timestamp recorded in the route data recorder; and a display processing unit for, when it is determined from the comparison by the route comparing unit that a close contact state existed, creating and displaying a message showing that a close contact state existed.

4 Claims, 10 Drawing Sheets

(56) References Cited

FOREIGN PATENT DOCUMENTS

| JP | 3559150 | B2 | 8/2004 |
| JP | 2005-025457 | A | 1/2005 |
| JP | 2006-053676 | A | 2/2006 |
| JP | 2009-086997 | A | 4/2009 |
| WO | WO2010023568 | A1 * | 3/2010 ............ G01C 21/34 |

* cited by examiner

| Timestamp | Position Information | |
| --- | --- | --- |
| | Latitude | Longitude |
| May, 2009 11:17 | 34 Degrees Plus 53 Minutes Plus 25.505 Seconds | 135 Degrees Plus 13 Minutes Plus 39.331 Seconds |
| May, 2009 11:18 | 34 Degrees Plus 53 Minutes Plus 25.180 Seconds | 135 Degrees Plus 13 Minutes Plus 46.781 Seconds |
| May, 2009 11:19 | 34 Degrees Plus 53 Minutes Plus 26.136 Seconds | 135 Degrees Plus 13 Minutes Plus 52.227 Seconds |
| May, 2009 11:20 | 34 Degrees Plus 53 Minutes Plus 26.567 Seconds | 135 Degrees Plus 13 Minutes Plus 53.881 Seconds |
| . | . | . |
| . | . | . |
| . | . | . |

| Type | Traffic Accident | |
|---|---|---|
| Name | Collision at XXX Intersection in YYY City | |
| Occurrence Conditions | A Passenger Car Which Had Made a Right Turn to North from East Collided with a Truck Which Had Travelled from West | |
| Time Period | Position Information | |
| | Latitude | Longitude |
| May, 2009 11:17 | 34 Degrees Plus 51 Minutes Plus 25.505 Seconds | 135 Degrees Plus 13 Minutes Plus 39.331 Seconds |
| May, 2009 11:25 | 34 Degrees Plus 51 Minutes Plus 25.180 Seconds | 135 Degrees Plus 14 Minutes Plus 46.781 Seconds |

MOVING ROUTE PROCESSING DEVICE AND INFORMATION PROVIDING SYSTEM USING THIS MOVING ROUTE PROCESSING DEVICE

FIELD OF THE INVENTION

The present invention relates to a moving route processing device which is applied to, for example, a navigation device or the like and which stores a moving route. It also relates to an information providing system using this moving route processing device.

BACKGROUND OF THE INVENTION

In recent years, type A influenza (H1N1) called a new type of influenza has spread around the world, which has become a social problem. Therefore, to prevent infection with the new type of influenza virus from spreading is a very important issue. Early detection of people infected with the virus is necessary to prevent the infection from spreading, and it is most effective to isolate people with suspected influenza virus infection before symptoms appear if possible. To this end, to technically detect a possibility of having coming into close contact with an infected person is desired.

Furthermore, when an incident, an accident, or a traffic accident (referred to as "something like an incident" from here on) occurs, witness testimony is very important because it results in the quick solution of the something like an incident, though a problem is that it is difficult to search for witnesses.

RELATED ART DOCUMENT

Patent Reference

Patent reference 1: Japanese Unexamined Patent Application Publication No. Hei 11-83531

In order to solve the above-mentioned conventional problems, it is necessary to store the moving routes of persons. Conventionally, an information providing device, for example, disclosed by patent reference 1, is known as a device for storing a route. This information providing device is provided with a display processing unit, a position detecting unit, a clock unit, a position storage unit, an area width input unit, a location familiarity degree calculating unit, and a location familiarity degree storage unit, calculates a degree of location familiarity from an area width and a position, and provides information according to the degree.

Because this information providing device is constructed as above, the device cannot detect a possibility of having coming into close contact with an infected person. Furthermore, because the information providing device cannot determine whether there is a match between the moving route of a person and the location where and the time period during which something like an incident occurred, i.e., cannot detect whether the person has witnessed the something like an incident. Then, the development of the technology is necessary to enable these detections.

The present invention is made in order to meet the above-mentioned request, and it is therefore an object of the present invention to provide a moving route processing device that can detect whether or not there is a possibility that a person has come into close contact with an infected person, and can detect whether or not there is a possibility that a person has witnessed something like an incident, and an information providing system using this moving route processing device.

SUMMARY OF THE INVENTION

In accordance with the present invention, there is provided a moving route processing device including: a route data creating unit for adding date and time information showing a current date and time to position information showing a current position to create route data with timestamp; a route data recorder for recording the route data with timestamp created by the route data creating unit; a communication processing unit for acquiring predetermined data from a database connected to a network; a route comparing unit for comparing the predetermined data acquired by the communication processing unit with the route data with timestamp recorded in the route data recorder; and a display processing unit for, when it is determined from the comparison by the route comparing unit that a close contact state existed, creating and displaying a message showing that a close contact state existed.

Because the moving route processing device in accordance with the present invention is constructed in such a way as to create and record route data with timestamp for the position information showing the current position, compare predetermined data acquired from the database connected to the network with the route data with timestamp to check to see whether or not a close contact state existed, and, when it is determined that a close contact state existed, creates and displays a message showing that a close contact state existed, the user can know that there is a possibility that the user was into close contact with a person infected with an epidemic disease, such as a new type of influenza, for example, and can know that there is a possibility that the user witnessed something like an incident.

EMBODIMENTS OF THE INVENTION

Hereafter, the preferred embodiments of the present invention will be explained in detail with reference to the drawings.

Embodiment 1

Figure 1:
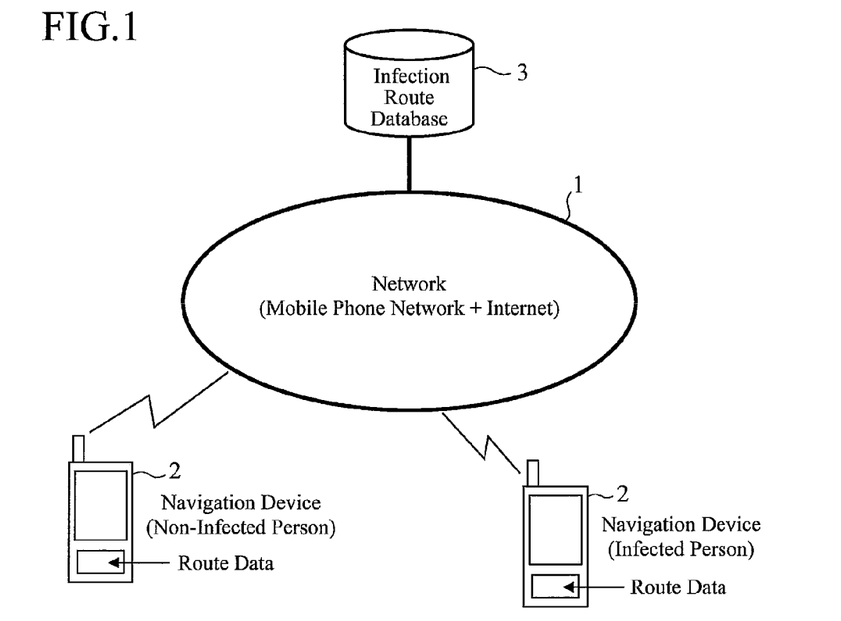
FIG. 1 is a view showing the structure of a navigation system to which an information providing system in accordance with Embodiment 1 of the present invention is applied.

FIG. 1 is a view showing the structure of a navigation system to which an information providing system in accordance with Embodiment 1 of the present invention is applied. This navigation system is provided with a network 1, a plurality of navigation devices 2, and an infection route database 3. Each navigation device 2 corresponds to a "moving route processing device" in accordance with the present invention.

The network 1 includes a mobile phone network and the Internet. Each of the plurality of navigation devices 2 is constructed in such a way as to be able to store route data with timestamp, and is connected to the Internet via the mobile phone network in the network 1. The plurality of navigation devices 2 include a navigation device owned by an infected person infected with an epidemic disease and a navigation device owned by a non-infected person who is not infected with any epidemic disease. The details of each navigation device 2 will be described below.

The Infection route database 3 corresponds to a "database" in accordance with the present invention, and stores infection route data. For example, this infection route database 3 is constructed as a part of a server, and is connected to the Internet included in the network 1.

Figure 2:
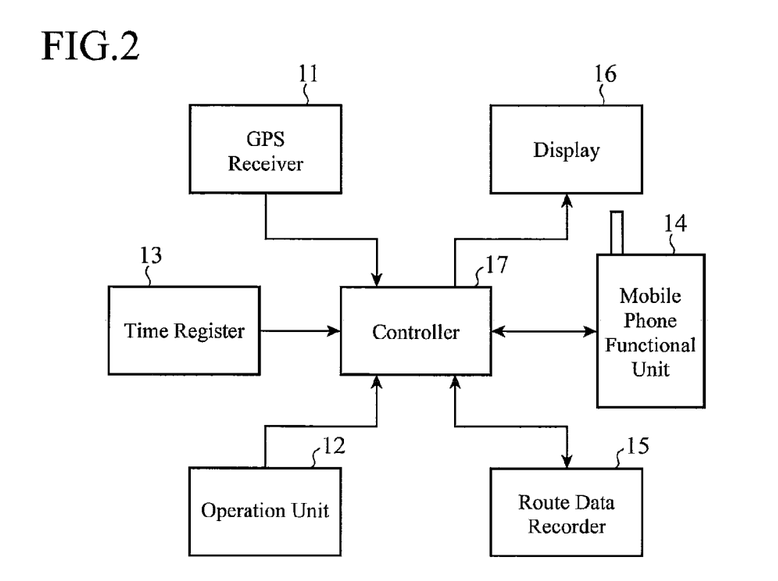
FIG. 2 is a block diagram showing the structure of a navigation device 2 which constructs the navigation system to which the information providing system in accordance with Embodiment 1 of the present invention is applied.

FIG. 2 is a block diagram showing the structure of each navigation device 2. Each navigation device 2 is provided with a GPS (Global Positioning System) receiver 11, an operation unit 12, a time register 13, a mobile phone functional unit 14, a route data recorder 15, a display 16, and a controller 17.

The GPS receiver 11 measures the position of the navigation device 2, and sends information showing the position to the controller 17 as position information. The position information is comprised of latitude information and longitude information. The operation unit 12 is comprised of operation buttons or a touch panel, for example. Operation information generated when a user operates this operation unit 12 is sent to the controller 17.

The time register 13 has a calendar function and a clocking function, and calculates the current date and time. Information showing the current date and time calculated by this time register 13 is sent to the controller 17 as date and time information. The mobile phone functional unit 14 is comprised of, for example, a mobile phone unit, and performs a process of connecting the navigation device 2 to the Internet via the mobile phone network in the network 1.

Figure 3:
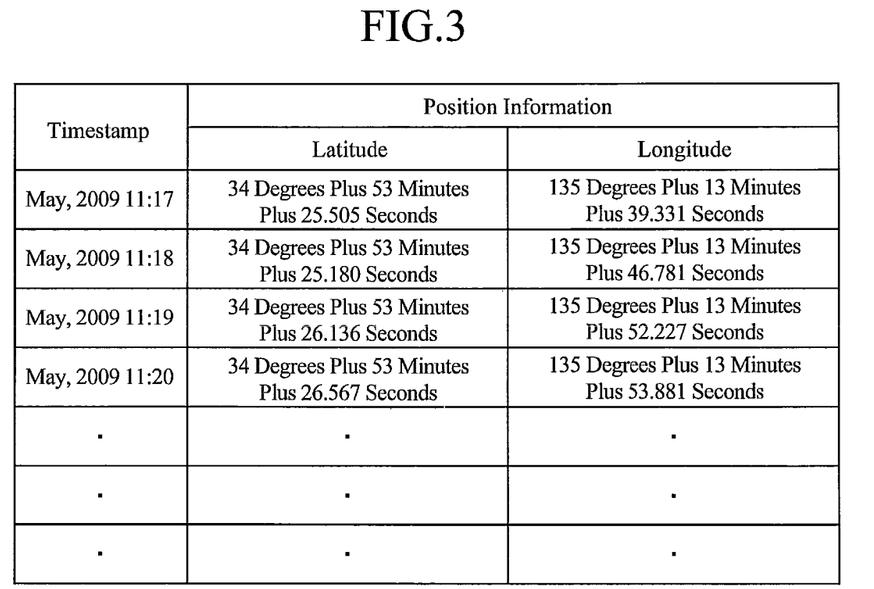
FIG. 3 is a view showing an example of route data with timestamp which is used in the navigation system to which the information providing system in accordance with Embodiment 1 of the present invention is applied.

The route data recorder 15 stores route data with timestamp which is sequentially sent thereto from the controller 17. The route data with timestamp stored in this route data recorder 15 is read by the controller 17. FIG. 3 is a view showing an example of the route data with timestamp stored in the route data recorder 15. Each route data with timestamp is comprised of a timestamp, which consists of a date and time, and position information.

The display 16 is comprised of an LCD (Liquid Crystal Display), for example, and displays a character string or a picture according to display data sent from the controller 17. The controller 17 controls the whole of the navigation device 2.

Figure 4:
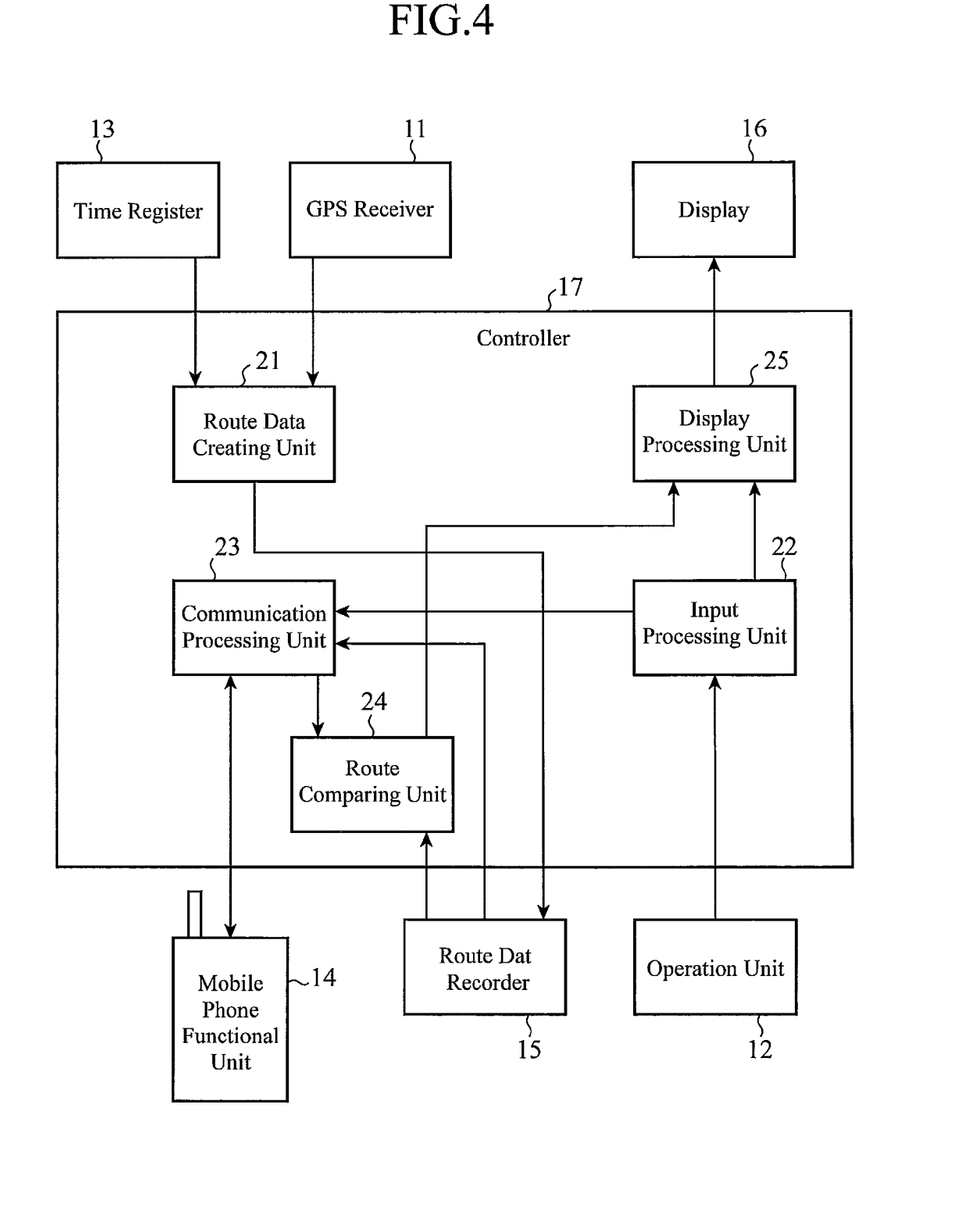
FIG. 4 is a block diagram showing the structure of a controller of each navigation device 2 of the navigation system to which the information providing system in accordance with Embodiment 1 of the present invention is applied.

FIG. 4 is a block diagram showing the structure of the controller 17. This controller 17 is provided with a route data creating unit 21, an input processing unit 22, a communication processing unit 23, a route comparing unit 24, and a display processing unit 25.

The route data creating unit 21 adds the date and time information acquired from the time register 13 to the position information acquired from the GPS receiver 11 to create route data with timestamp. The route data creating unit 21 also writes this route data in the route data recorder 15. The input processing unit 22 performs a predetermined process on the operation information sent from the operation unit 12, and sends the operation information to the communication processing unit 23 and the display processing unit 25.

The communication processing unit 23 controls communications which are carried out between the navigation device 2 and the external infection route database 3 via the mobile phone functional unit 14 and the network 1. The route comparing unit 24 compares route data with timestamp which are acquired from the infection route database 3 by the communication processing unit 23 with the route data with timestamp which are recorded in the route data recorder 15 to determine whether or not a state in which their locations coincided with each other existed as a close contact state. The result of the comparison (determination result) by this route comparing unit 24 is sent to the display processing unit 25.

When it is determined from the comparison by the route comparing unit 24 that a state in which their locations coincided with each other existed, the display processing unit 25 creates a warning message showing that a state in which their locations coincided with each other existed, and sends the warning message to the display 16. As a result, the warning message is displayed on the display 16.

Next, operations of the navigation system in accordance with Embodiment 1 of the present invention constructed as above will be explained. First, the route data acquisition operation will be explained with reference to a flow chart shown in FIG. 5.

Figure 5:
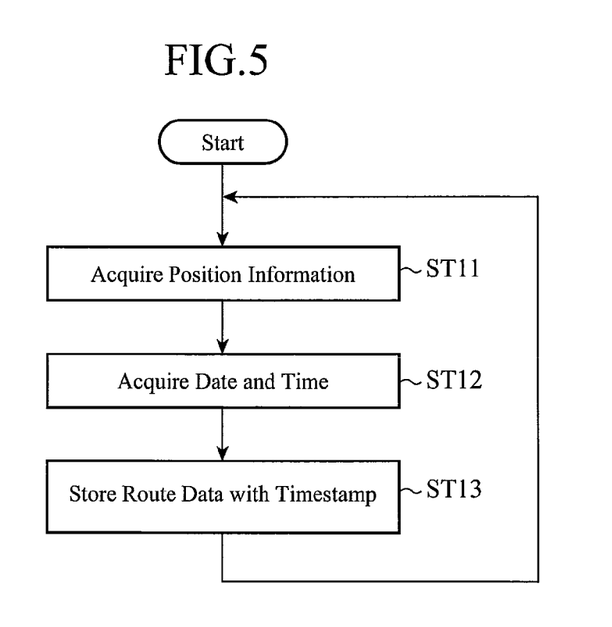
FIG. 5 is a flow chart showing a route data acquisition operation performed by the navigation system to which the information providing system in accordance with Embodiment 1 of the present invention is applied.

When the route data acquisition operation is started, the position information is acquired first (step ST11). More specifically, the route data creating unit 21 of the controller 17 acquires the position information from the GPS receiver 11. The date and time information is then acquired (step ST12). More specifically, the route data creating unit 21 acquires the date and time information from the time register 13.

The route data with timestamp is then stored (step ST13). More specifically, the route data creating unit 21 pairs the position information acquired from the GPS receiver 11 in step ST11 with the date and time information acquired from the time register 13 in step ST12 to create route data with timestamp as shown in FIG. 3 and write the route data in the route data recorder 15. Then, each navigation device 2 returns the sequence to step ST11 and repeats the above-mentioned process at predetermined intervals of, for example, 1 minute. Accordingly, the route data with timestamp as shown in FIG. 3 is sequentially stored in the route data recorder 15.

Figure 6:
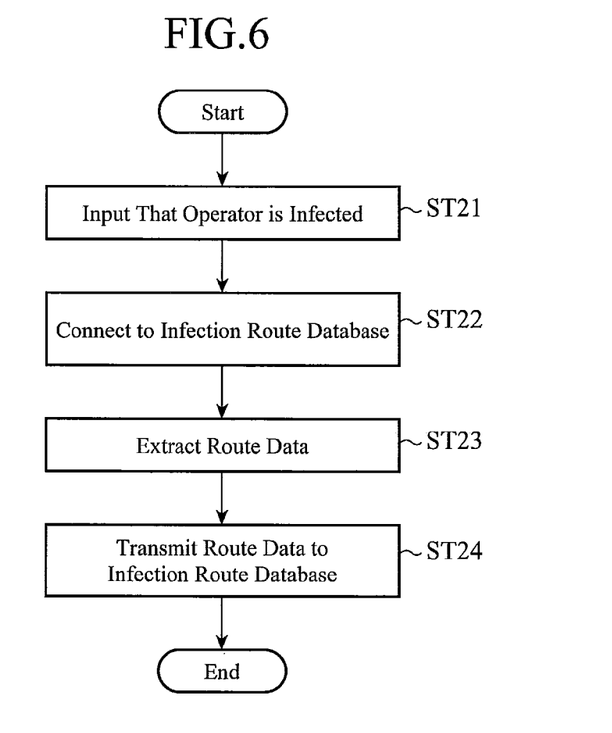
FIG. 6 is a flowchart showing an operation when a user is an infected person in the navigation system to which the information providing system in accordance with Embodiment 1 of the present invention is applied.

Next, an operation performed by this navigation system when it becomes clear that the user of a navigation device 2 has been infected with an epidemic disease will be explained with reference to a flow chart shown in FIG. 6.

When it becomes clear that the user has been infected with an epidemic disease, the user or another operator of the navigation device 2 operates the operation unit 12 of the navigation device 2 to input that he or she has been infected with an epidemic disease (step ST21). Information, which is inputted from this operation unit 12, shows that the user has been infected with an epidemic disease. And it is sent to the input processing unit 22 of the controller 17 as operation information.

The navigation device 2 is then connected to the infection route database (step ST22). More specifically, the input processing unit 22 sends the operation information showing that the user has been infected with an epidemic disease to the communication processing unit 23. In response to this operation information, the communication processing unit 23 connects the navigation device 2 to the infection route database 3 on the Internet via the mobile phone network in the network 1 by way of the mobile phone functional unit 14.

The route data are then extracted (step ST23). More specifically, the communication processing unit 23 of the controller 17 extracts the route data with timestamp from the route data recorder 15.

The route data are then transmitted to the infection route database 3 (step ST24). More specifically, the communication processing unit 23 transmits the route data with timestamp extracted from the route data recorder 15 in step ST23 to the infection route database 3 in the network 1 by way of the mobile phone functional unit 14 as infection route data. After the process at the time when it becomes clear that the user has been infected with an epidemic disease is carried out in this way, the process is ended.

The user is allowed to input a time period from the operation unit 12, and the communication processing unit 23 can be constructed in such a way as to transmit the route data associated with the inputted time period. Furthermore, the navigation system can be constructed in such a way as to, when infection route data is stored in the infection route database 3, broadcast that the infection route data is stored in the infection route database through television broadcasting or radio broadcasting, or notify any user whose e-mail address is registered with the navigation system in advance by e-mail that the infection route data is stored in the infection route database 3.

Figure 7:
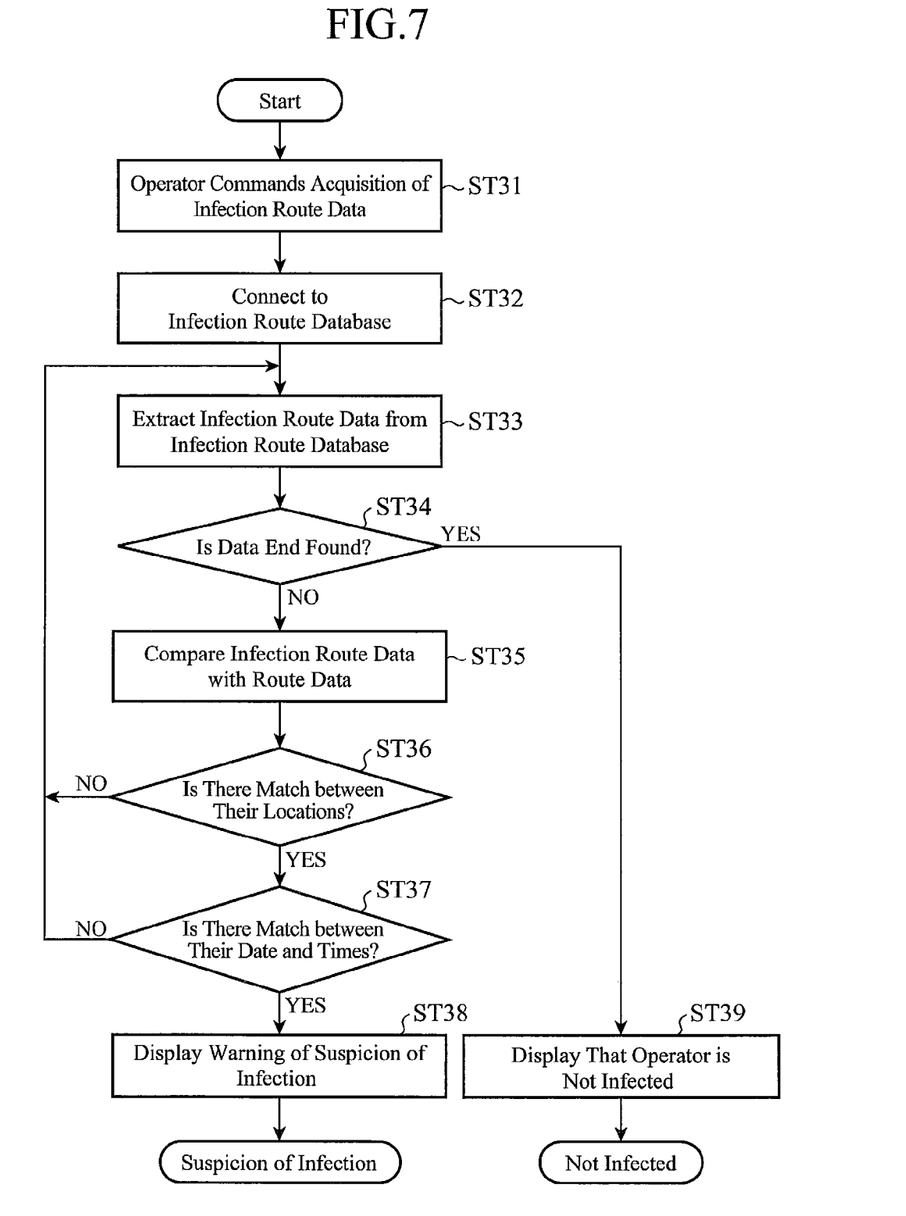
FIG. 7 is a flow chart showing an operation when the existence of an infected person is known in the navigation system to which the information providing system in accordance with Embodiment 1 of the present invention is applied.

Next, an operation of the navigation device 2 owned by a user (non-infected person) who has known the existence of a person who has been infected with an epidemic disease in this navigation system will be explained with reference to a flow chart shown in FIG. 7.

When it is broadcast through television broadcasting or radio broadcasting that infection route data is stored in the infection route database 3 or when the user is notified that infection route data is stored in the infection route database 3 by e-mail after the infection route data has been stored in the infection route database 3, the navigation device 2 is commanded to acquire the infection route data (step ST31). More specifically, the operator operates the operation unit 12 to command the navigation device 2 to acquire the infection route data.

The navigation device 2 is then connected to the infection route database 3 (step ST32). More specifically, the input processing unit 22 sends the operation information to command the navigation device 2 to acquire the infection route data sent from the operation unit 12 to the communication processing unit 23. In response to this operation information, the communication processing unit 23 connects the navigation device 2 to the infection route database 3 on the Internet via the mobile phone network in the network 1 by way of the mobile phone functional unit 14.

The infection route data is then extracted from the infection route database 3 (step ST33). More specifically, the communication processing unit 23 of the controller 17 extracts the infection route data from the infection route database 3 via the mobile phone functional unit 14 and the network 1.

Whether or not a data end is found is then checked to see (step ST34). More specifically, the communication processing unit 23, in step ST33, checks to see whether it has succeeded in extracting the infection route data from the infection route database 3. When, in this step ST34, not finding a data end, that is, when having succeeded in extracting the infection route data, the communication processing unit 23 sends the extracted infection route data to the route comparing unit 24.

A comparison between the infection route data and the route data is then made (step ST35). More specifically, the route comparing unit 24 compares the infection route data extracted in step ST33 with the route data stored in the route data recorder 15.

Then, it is checked to see whether or not their locations coincided with each other from the comparison in above-mentioned step ST35 (step ST36). More specifically, the route comparing unit 24 checks to see whether or not there is a match between a latitude and a longitude which are included in the infection route data, and a latitude and a longitude which are included in the route data stored in the route data recorder 15. When it is determined in this step ST36 that there is no match between their locations, the navigation device 2 returns the sequence to step ST33 and performs the process on the next infection route data.

In contrast, when it is determined in this step ST36 that there is a match between their locations, it is checked to see whether there is a match between their dates and times (step ST37). More specifically, the route comparing unit 24 checks to see whether or not there is a match between a date and time included in the infection route data and a date and time included in the route data stored in the route data recorder 15. When it is determined in this step ST37 that there is no match between their dates and times, the navigation device 2 returns the sequence to step ST33 and performs the process on the next infection route data.

In contrast, when it is determined in step ST37 that there is a match between their dates and times, it is determined that the user of the navigation device 2 is a person who has come into close contact with the infected person, and a warning of suspicion of infection is displayed (step ST38). More specifically, the route comparing unit 24 sends data showing the warning of suspicion of infection to the display processing unit 25, and the display processing unit 25 displays a warning message "You are suspected of having become infected with an epidemic disease" on the display 16, for example, while displaying the location and the date and time which constitute grounds for determining that the user is a person who has come into close contact with the infected person. Then, the process is ended.

In this case, the navigation device 2 can be constructed in such a way as to display the location on a map by using map data stored in a not-shown map recorder. According to this structure, there is provided an advantage of enabling the user to easily recognize the location where he or she was in contact with the infected person.

When, in above-mentioned step ST34, finding a data end, that is, when having failed in extracting any infection route data, the navigation system recognizes that the process on all the infection route data is completed, but there exists no infection route data having a location and a date and time matching those of the route data, and it is displayed that the user is not infected with any epidemic disease (step ST39). More specifically, the route comparing unit 24 sends data showing that the user is not infected with any epidemic disease to the display processing unit 25, and the display processing unit 25 displays a message "Not infected" on the display 16, for example. Then, the process is ended.

As previously explained, the navigation system in accordance with Embodiment 1 of the present invention can know that there is a possibility that a user has been infected with an epidemic disease, such as a new type of influenza, at an early time, and enables the user to get medical treatment at an early time. Furthermore, because the navigation system enables the user to know that there is a possibility of having become infected with an epidemic disease before symptoms appear, the navigation system can prevent infection with an epidemic disease from spreading (pandemic).

Embodiment 2

Figure 8:
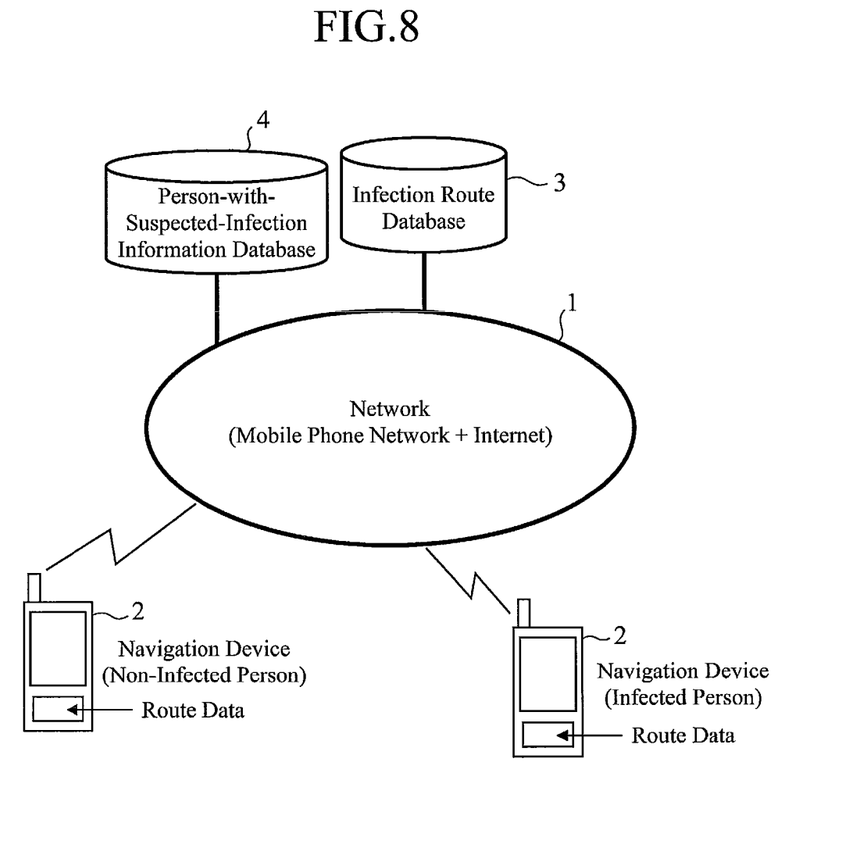
FIG. 8 is a view showing the structure of a navigation system to which an information providing system in accordance with Embodiment 2 of the present invention is applied.

FIG. 8 is a view showing the structure of a navigation system to which an information providing system in accordance with Embodiment 2 of the present invention is applied. This navigation system is constructed in such a way that a person-with-suspected-infection information database 4 is added to the navigation system in accordance with Embodiment 1 shown in FIG. 1.

The person-with-suspected-infection information database 4 corresponds to "another database" in accordance with the present invention, and stores information about persons with suspected infection. This person-with-suspected-infection information database 4 is connected to the Internet in the network 1.

Figure 9:
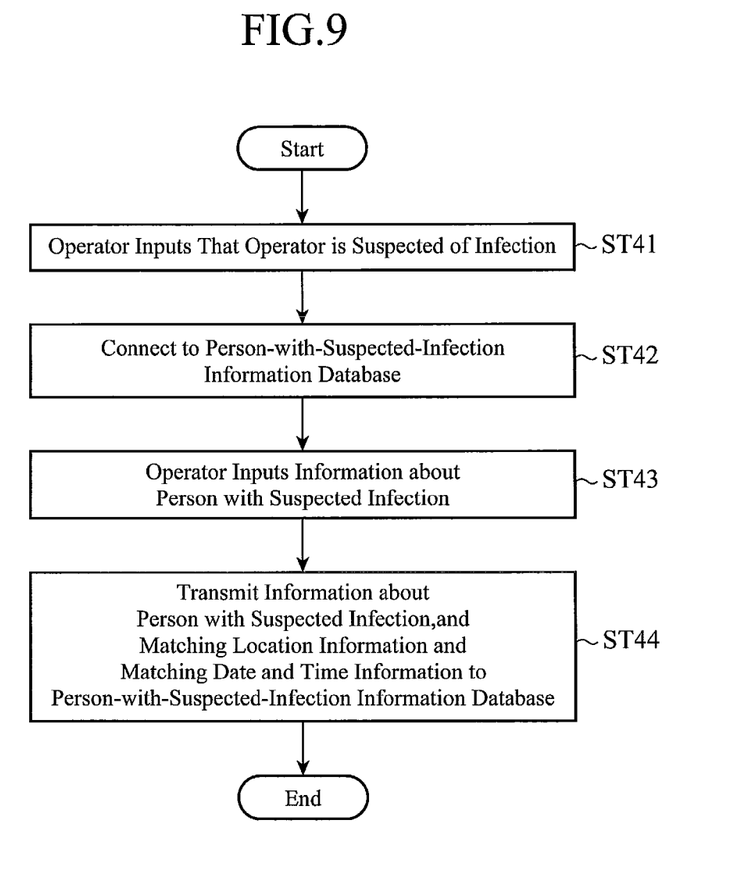
FIG. 9 is a flow chart showing operations of the navigation system to which the information providing system in accordance with Embodiment 2 of the present invention is applied.

Next, operations of the navigation system in accordance with Embodiment 2 of the present invention constructed as above will be explained with reference to the flow chart shown in FIG. 9.

When the user of a navigation device 2 judges that he or she is suspected of having become infected with an epidemic disease, the user operates the operation unit 12 of the navigation device 2 first to input that he or she is suspected of infection (step ST41). Information, which is inputted from this operation unit 12, shows that the user is suspected of infection. And it is sent to an input processing unit 22 of a controller 17 as operation information.

The navigation device 2 is then connected to the person-with-suspected-infection information database (step ST42). More specifically, the input processing unit 22 sends the operation information showing that the user is suspected of infection to the communication processing unit 23. In response to this operation information, the communication processing unit 23 connects the navigation device 2 to the person-with-suspected-infection information database 4 on the Internet via the mobile phone network in the network 1 by way of the mobile phone functional unit 14.

Information on person with suspected infection is then inputted (step ST43). More specifically, the operator inputs information about person with suspected infection by using the operation unit 12. The information about person with suspected infection can consist of the operator's address, name, telephone number, place of employment or place of school, and commuting route or family structure, for example. When the information about person with suspected infection is inputted from the operation unit 12, the input processing unit 22 sends the inputted information about person with suspected infection to a display processing unit 25, and the display processing unit displays the received information about person with suspected infection on a display 16. As a result, the operator can check the inputted information.

The information about person with suspected infection, and matching location information and matching date and time information are then transmitted to the person-with-suspected-infection information database 4 (step ST44). More specifically, the input processing unit 22 sends the inputted information about person with suspected infection to the communication processing unit 23, and the communication processing unit 23 transmits the information about person with suspected infection, and the location where and the date and time when it is determined that the user was in close contact with a person infected with an epidemic disease to the person-with-suspected-infection information database 4 on the network 1 via the mobile phone functional unit 14. The process is then ended.

When the information about person with suspected infection is inputted to the person-with-suspected-infection information database 4 through the above-mentioned process, someone like an operator of an administrative organ can use a navigation device 2 or a personal computer to browse the information about person with suspected infection, and the location where and the date and time when it is determined that the user was in close contact with a person infected with an epidemic disease.

Although writing data in the above-mentioned person-with-suspected-infection information database 4 is allowed for ordinary civilians, the process of reading data from the person-with-suspected-infection information database is encrypted and is protected with a password or the like for private information protection so that the reading process is limited to the administrative organ.

The navigation system in accordance with above-mentioned Embodiment 2 is constructed in such away that when an operator judges that he or she is suspected of infection, he or she inputs information showing that he or she is suspected of infection from the operation unit 12, and then inputs information about person with suspected infection manually. As an alternative, the navigation system can be constructed in such a way that each navigation device 2 inputs information about the owner of the navigation device 2 in advance, and, when it is determined that the owner of a navigation device 2 is suspected of infection, the controller 17 of the navigation device 2 transmits the information about person with suspected infection to the person-with-suspected-infection information database 4 automatically.

As previously explained, because the navigation system in accordance with Embodiment 2 of the present invention enables an administrative organ to grasp the conditions of people with suspected infection with a new type of influenza or the like, the navigation system can prevent infection with an epidemic disease from spreading (pandemic).

Embodiment 3

Figure 10:
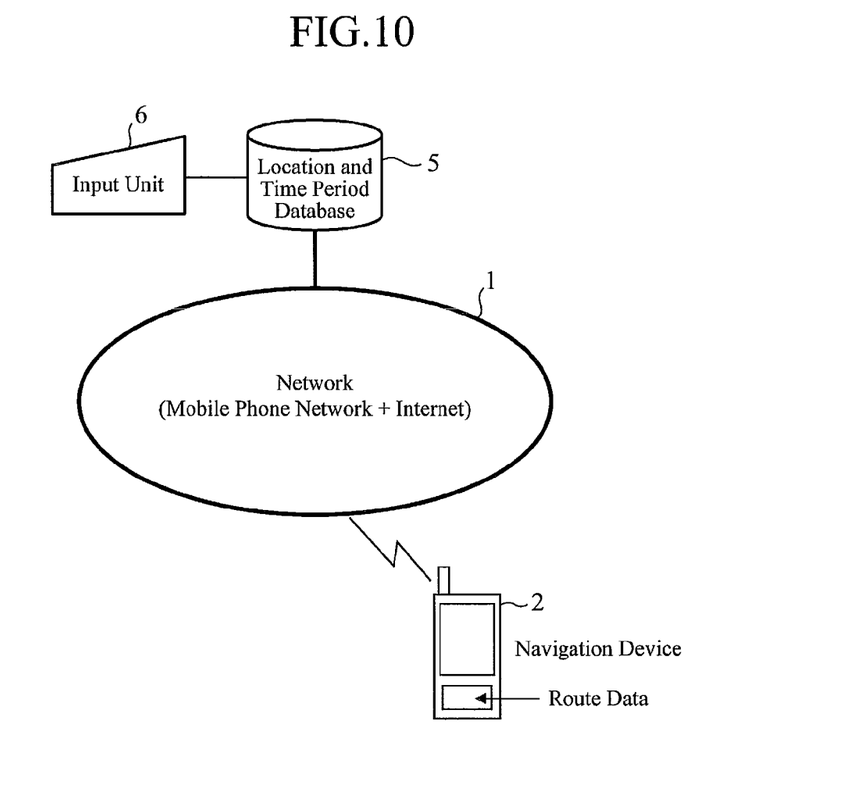
FIG. 10 is a view showing the structure of a navigation system to which an information providing system in accordance with Embodiment 3 of the present invention is applied.

FIG. 10 is a view showing the structure of a navigation system to which an information providing system in accordance with Embodiment 3 of the present invention is applied. This navigation system is provided with a network 1, a navigation device 2, a location and time period database 5, and an input unit 6. The structures and operations of the network 1 and the navigation device 2 are the same as those of the navigation system in accordance with above-mentioned Embodiment 1. Although FIG. 10 shows a case in which only the navigation device 2 is connected to the network 1, the number of navigation devices 2 connected to the network 1 is arbitrary.

The location and time period database 5 stores plural pieces of location and time period data each showing the location where and the time period during which something like an incident occurred, and is connected to the Internet in the network 1. The input unit 6 inputs location and time period data to the location and time period database 5.

Figure 11:
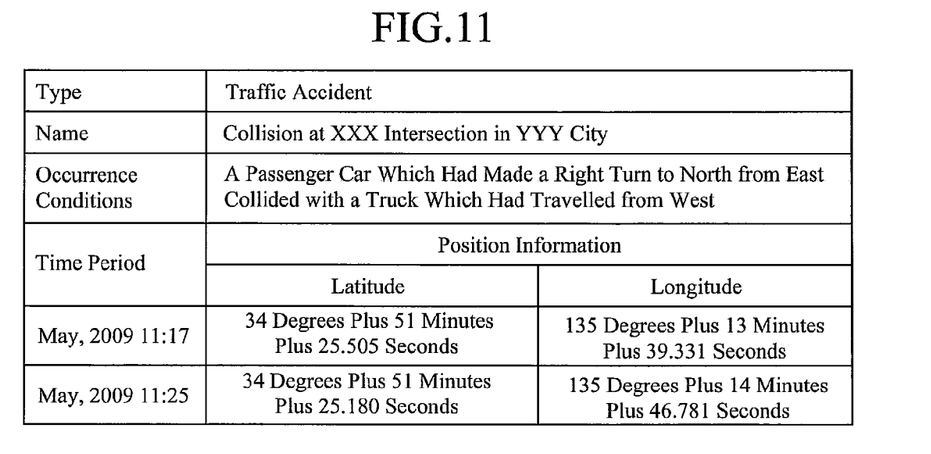
FIG. 11 is a view showing an example of location and time period data which is used in the navigation system to which the information providing system in accordance with Embodiment 3 of the present invention is applied.

FIG. 11 is a view showing an example of each piece of location and time period data stored in the location and time period database 5. Each piece of location and time period data is comprised of the type of something like an incident, an incident name, an accident name or a traffic accident name, occurrence condition data, a time period, and position information. The time period shows a time period during which the something like an incident occurred, and is expressed by a start time and an end time. The position information is comprised of latitudes and longitudes. The latitudes are expressed by the latitude of a northernmost end and the latitude of a southernmost end. The longitudes are expressed by the longitude of an easternmost end and the longitude of a westernmost end. The region of the quadrangle enclosed by these four points is the location where the something like an incident occurred.

Next, operations of the navigation system in accordance with Embodiment 3 of the present invention constructed as above will be explained. First, an operation of inputting location and time period data will be explained with reference to a flow chart shown in FIG. 12.

Figure 12:
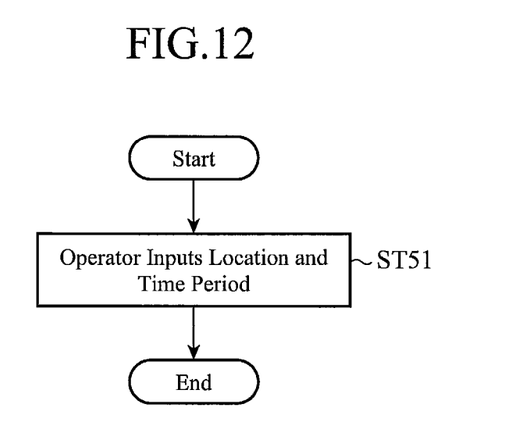
FIG. 12 is a flow chart showing an operation of inputting location and time period data to the navigation system to which the information providing system in accordance with Embodiment 3 of the present invention is applied.

When something like an incident occurs, the location and the time period of the something are inputted (step ST51). More specifically, an operator of the navigation system operates the input unit 6 to input the location where and the time period during which the something like an incident occurred to the location and time period database 5. At this time, the operator also inputs the type of the something like an incident, an incident name, an accident name or a traffic accident name, and occurrence conditions. Then, the navigation system ends the operation of inputting the location and time period data.

The navigation system can be constructed in such a way as to, after the location and time period data are stored in the location and time period database 5, broadcast that the location and time period data are stored in the location and time period database through television broadcasting or radio broadcasting, or notify any user whose e-mail address is registered with the navigation system in advance by e-mail that the location and time period data are stored in the location and time period database.

Figure 13:
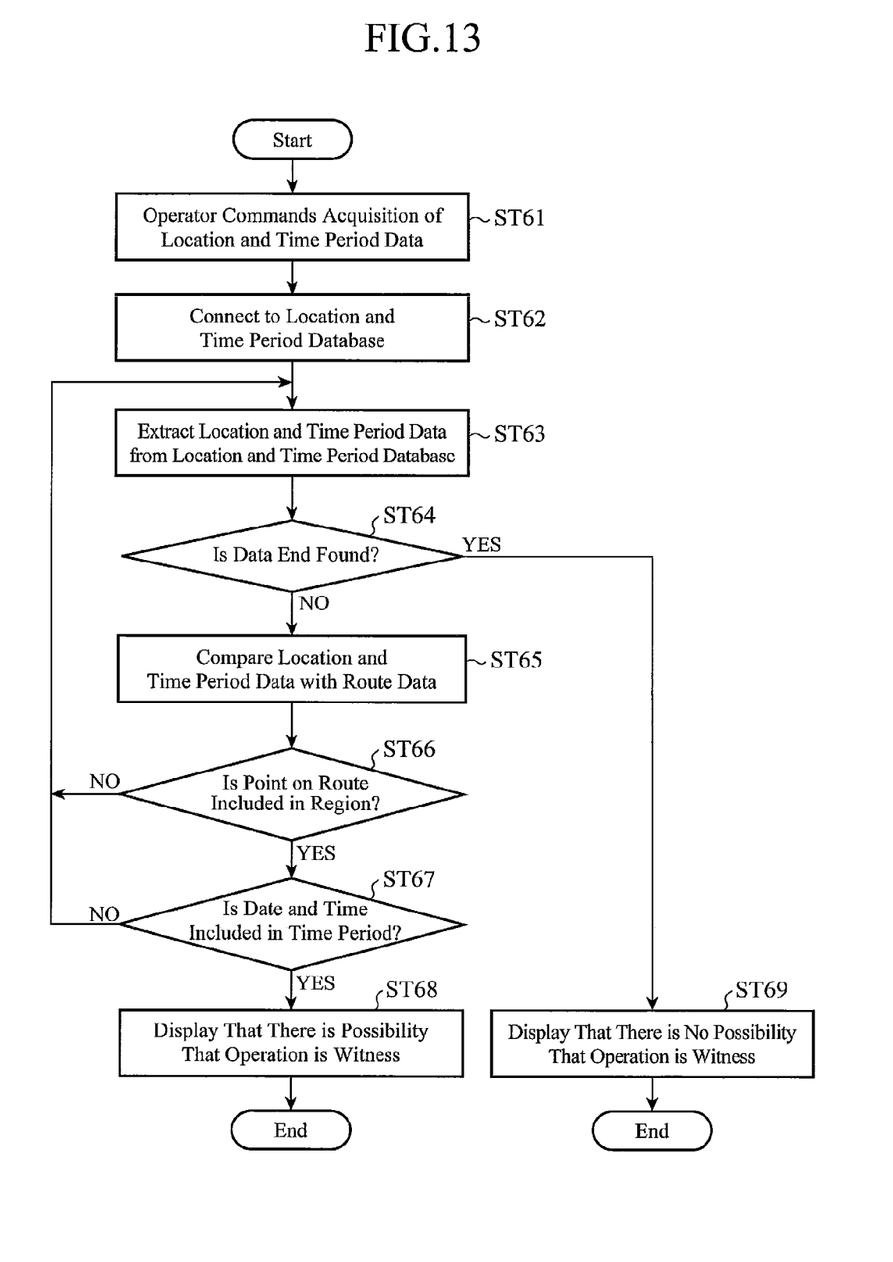
FIG. 13 is a flow chart showing an operation when the storage of location and time period data is broadcast in the navigation system to which the information providing system in accordance with Embodiment 3 of the present invention is applied.

Next, an operation of this navigation system when the navigation system broadcasts that the location and time period data are stored in the location and time period database through television broadcasting or radio broadcasting, or notifies any registered user by e-mail that the location and time period data are stored in the location and time period database 5 after the location and time period data are stored in the location and time period database 5 will be explained with reference to a flow chart shown in FIG. 13.

When the navigation system broadcasts the occurrence of something like an incident, acquisition of the location and time period data is commanded first (step ST61). More specifically, the operator of the navigation device 2 operates the operation unit 12 to command acquisition of the location and time period data.

The navigation device 2 is then connected to the location and time period database 5 (step ST62). More specifically, an input processing unit 22 sends operation information to command acquisition of the route data to a communication processing unit 23. In response to this operation information, the communication processing unit 23 connects the navigation device 2 to the location and time period database 5 on the Internet via the mobile phone network in the network 1 by way of a mobile phone functional unit 14.

The location and time period data are then extracted from the location and time period database 5 (step ST63). More specifically, the communication processing unit 23 of a controller 17 extracts the location and time period data from the location and time period database 5 via the mobile phone functional unit 14.

Whether or not a data end is found is then checked to see (step ST64). More specifically, the communication processing unit 23, in step ST63, checks to see whether it has succeeded in extracting the location and time period data. When, in this step ST64, not finding a data end, that is, when having succeeded in extracting the location and time period data, the communication processing unit 23 sends the location and time period data to a route comparing unit 24.

A comparison between the location and time period data and the route data is then made (step ST65). More specifically, the route comparing unit 24 compares the location and time period data extracted in step ST63 with the route data stored in a route data recorder 15.

Then, it is checked to see whether or not a point on the route is included in the region from the comparison in above-mentioned step ST65 (step ST66). More specifically, the route comparing unit 24 checks to see whether or not a point shown by a latitude and a longitude which are included in the route data stored in the route data recorder 15 is included in the region of the quadrangle formed of the latitudes and longitudes which are included in the location and time period data. When it is determined in this step ST66 that there is no match between their locations, the navigation device 2 returns the sequence to step ST63 and performs the process on the next location and time period data.

In contrast, when it is determined in this step ST66 that there is a match between their locations, it is checked to see whether a date and time of the route data is included within the time period (step ST37). More specifically, the route comparing unit 24 checks to see whether or not a timestamp of the route data, i.e., a date and time included in the route data stored in the route data recorder 15 is included within the time period included in the location and time period data. When it is determined in this step ST37 that any date and time included in the route data is not included within the time period, the navigation device 2 returns the sequence to step ST33 and performs the process on the next location and time period data.

In contrast, when it is determined in step ST67 that a date and time included in the route data is included within the time period, it is displayed that there is a possibility that the user of the navigation device 2 is a witness (step ST68). More specifically, the route comparing unit 24 transmits information showing that there is a possibility that the user of the navigation device 2 is a witness to a display processing unit 25, and the display processing unit 25 displays a message showing "You may be a witness" on a display 16, for example, while displaying the location, the date and time, the type of the something like an incident, the incident name, the accident name or the traffic accident name, and the occurrence conditions. Then, the process is ended.

In this case, the navigation device 2 can be constructed in such a way as to display the location on a map by using map data stored in a not-shown map recorder. According to this structure, there is provided an advantage of enabling the user to easily recognize the location where he or she may witness the something like an incident.

When, in above-mentioned step ST64, finding a data end, that is, when having failed in extracting any location and time period data, the navigation device 2 recognizes that the process on all the location and time period is completed, but there exists no location and time period data having a region in which a point on the route is included and a time period in which a date and time of the route data is included, and it is displayed that there is no possibility that the user is a witness (step ST69). More specifically, the route comparing unit 24 transmits that there is no possibility that the user is a witness to the display processing unit 25, and the display processing unit 25 displays a message showing that "There is no possibility that you are a witness" on the display 16, for example. Then, the process is ended.

As previously explained, because the navigation system in accordance with Embodiment 3 of the present invention enables the user to recognize that there is a possibility that he or she is a witnesses of something like an incident, the navigation system can be used for quick solution of an incident, investigation of causes of an accident or investigation of causes of a traffic accident.

Although in the navigation system in accordance with either of above-mentioned Embodiments 1 to 3 the network including the mobile phone network and the Internet is used, a network not including a mobile phone network but including only the Internet can be alternatively used.

Furthermore, although in the navigation system in accordance with either of above-mentioned Embodiments 1 to 3 each navigation device 2 is constructed in such a way as to access the Internet via the mobile phone network by using the mobile phone functional unit 14, each navigation device 2 can be constructed in such a way as to include an Internet connection functional unit for accessing the Internet, instead of the mobile phone functional unit 14, and access the Internet directly. As an alternative, each navigation device 2 can be constructed in such a way as to include a USB connection function, instead of the mobile phone functional unit 14, and connect with a home personal computer via USB to access the Internet from the personal computer.

Furthermore, although in the navigation system in accordance with either of above-mentioned Embodiments 1 to 3 each navigation device 2 is constructed in such a way as to display a message warning the presence or absence of infection or a message showing whether or not there is a possibility that the user is a witness as a result of comparison with the user's moving route, each navigation device 2 can be constructed in such a way as to include an audio output unit, and output each of these messages by voice. Each navigation device 2 can also be constructed in such a way as to transmit each of the messages to another distant location via a communication network.

Although in the navigation system in accordance with either of above-mentioned Embodiments 1 to 3 the case in which an epidemic disease, an incident, an accident, or a traffic accident occurred is explained, the present invention is not limited to this case. The present invention can be applied to various devices which are constructed in such a way as to compare various data with route data to provide the user with the results of the comparison.

Industrial Applicability

The present invention can be used for, for example, a system which deals with epidemic diseases, such as new types of influenza, at an early time, or a system which is used for quick solution of an incident, investigation of causes of an accident, or investigation of causes of a traffic accident.

The invention claimed is:

1. A moving route processing device comprising:
    a route data creating unit for adding date and time information showing a current date and time to position information showing a current position to create each of a plurality of route data entries with respective timestamps;
    a route data recorder for recording route data comprising the route data entries with timestamps created by said route data creating unit;
    a communication processing unit for acquiring predetermined data from a database connected to a network, wherein the predetermined data acquired by communication processing unit from the database comprises route data with at least one timestamp showing a moving route of a person infected with an epidemic disease;
    a route comparing unit for comparing the predetermined data acquired by said communication processing unit with at least part of the route data with timestamps recorded in said route data recorder; and
    a display processing unit for, when it is determined from the comparison by said route comparing unit that a close contact state existed, creating and displaying a message showing that a close contact state existed.

2. The moving route processing device according to claim 1, wherein the communication processing unit acquires location and time period data showing a location where and a time period during which something like an incident occurred from the database connected to the network.

3. The moving route processing device according to claim 1, wherein the route comparing unit compares time information provided within the predetermined data and the at least part of the route data with timestamps recorded in the route data recorder.

4. The moving route processing device according to claim 1, wherein the route data with timestamps recorded by the route data recorder shows a route previously traveled by the moving route processing device.

* * * * *